United States Patent
Tamaoki et al.

(10) Patent No.: US 6,190,520 B1
(45) Date of Patent: Feb. 20, 2001

(54) IMPURITY MEASURING DEVICE

(75) Inventors: Makiko Tamaoki, Yokohama; Yumi Sasaki, Kamakura, both of (JP)

(73) Assignee: Kabushiki Kaisha Toshiba, Kawasaki (JP)

( * ) Notice: Under 35 U.S.C. 154(b), the term of this patent shall be extended for 0 days.

(21) Appl. No.: 09/225,221

(22) Filed: Jan. 4, 1999

Related U.S. Application Data

(62) Division of application No. 08/758,575, filed on Dec. 3, 1996, now Pat. No. 5,882,504.

(30) Foreign Application Priority Data

Dec. 5, 1995 (JP) ...................................................... 7-316499

(51) Int. Cl.$^7$ ............................................... G01N 27/26
(52) U.S. Cl. ...................... 204/434; 204/400; 205/775; 205/789.5; 205/790
(58) Field of Search ................................... 204/400, 434; 205/775, 789.5, 790

(56) References Cited

U.S. PATENT DOCUMENTS

| | | | |
|---|---|---|---|
| 2,544,802 | 3/1951 | Notvest | 205/790 |
| 2,566,676 | 9/1951 | Rabbitts | 204/434 |
| 2,773,020 | 12/1956 | Offutt et al. | 205/789.5 |
| 3,427,238 | 2/1969 | Myers et al. | 204/405 |
| 3,919,067 | * 11/1975 | Carson et al. | 204/412 |
| 4,090,926 | 5/1978 | Matson | 204/413 |
| 4,146,436 | 3/1979 | Kellermann et al. | 204/434 |
| 4,416,736 | 11/1983 | Huber | 204/434 |

FOREIGN PATENT DOCUMENTS 7-311050   11/1995   (JP) .

OTHER PUBLICATIONS

Metal Finishing Guidebook Directory, 43$^{rd}$ Annual Edition, 1975 Month Unavailable, pp. 684–686.
Lowenheim, "Electroplating," 1978 Month Unavailable, pp. 139 and 156.

* cited by examiner

*Primary Examiner*—T. Tung
(74) *Attorney, Agent, or Firm*—Finnegan, Henderson, Farabow, Garrett & Dunner, L.L.P.

(57) ABSTRACT

A first solution is brought into contact with a surface of a sample so that impurities, which exist in the sample or on the surface of the sample, and the sample are dissolved in the first solution, and a voltage is applied across electrodes by putting the electrodes into the first solution so that substances including the impurities are deposited on the surface of the electrodes, and the deposited impurities are dissolved in a second solution so that impurities dissolved in the second solution are measured. As a result, an impurity measuring method and an impurity measuring device, which are capable of measuring a very small amount of impurities with high sensitivity, which exist in the sample or on the surface of the sample, are provided.

2 Claims, 3 Drawing Sheets

IMPURITY MEASURING DEVICE

This is a division of application Ser. No. 08/758,575, filed Dec. 3, 1996 (now U.S. Pat. No. 5,882,504), which is incorporated herein by reference.

BACKGROUND OF THE INVENTION

1. Field of the Invention

The present invention relates to a method of measuring a small amount of impurities and an impurity measuring device.

2. Description of the Related Art

In a process of manufacturing a semiconductor apparatus, metallic impurities, such as Na, K and Fe, are undesirably mixed to a thin film such as a polycrystal silicon film which is formed in or on a semiconductor substrate. It is generally known that if a very small amount of such metallic impurities are mixed, a bad influence is exerted on an electric characteristic of the semiconductor apparatus. For this reason, in order to improve the electric characteristic of the semiconductor apparatus, it is necessary to accurately grasp an amount of the mixed metallic impurities in each manufacturing steps and take measures to suppress the mixing of impurities.

The following explains a conventional device and method of measuring an amount of metallic impurities existing in and on a thin film which is formed in or on a semiconductor substrate or on a surface of a semiconductor substrate on reference to FIGS. 4, 5A and 5B.

FIG. 4 is a perspective view which shows an arrangement of a conventional impurity measuring device, FIG. 5A is a top view of the conventional impurity measuring device of FIG. 4, and FIG. 5B is a cross sectional view taken along line VB—VB of the impurity measuring device. The conventional impurity measuring device is composed of a substrate holding stand 1, a frame 2 and four screws 3. The substrate holding stand 1 has a concave section for holding a semiconductor substrate 10, and a depth of the concave section is smaller than a thickness of the semi-conductor substrate 10. The frame 2 has an opening which penetrate the frame 2 at its center portion, and a diameter of the opening is smaller than a diameter of the semiconductor substrate 10. Moreover, the substrate holding stand 1 and the frame 2 respectively have holes for the screws 3 at each corner. The holding stand 1, the frame 2 and the four screws 3 are made of, for example, Teflon.

In the conventional impurity measuring method, first, the semiconductor substrate 10 on which a film is not formed or the semiconductor substrate 10 on which a thin film is formed, is placed on the concave section of the holding stand 1, then the frame 2 is placed on the semiconductor substrate 10, and the corners of the holding stand 1 are fitted on the corresponding corners of the frame 2 so that the corners are fastened with the screws 3. As a result, the frame 2 is fixed tight on the semiconductor substrate 10. Next, a solution 4, which dissolves the semiconductor substrate 10 or the thin film on the semiconductor substrate, is poured into a cavity formed by the opening of the frame 2 and the substrate 10, and the semiconductor substrate 10 or the thin film of the semiconductor substrate are dissolved by the solution 4. Then, an impurity, which exists in the thin film and on the surface of the thin film formed in or on the semiconductor substrate 10 or on the surface of the semiconductor substrate 10, exists in the solution 4 as ion. Thereafter, the impurity contained in the solution 4 is measured by, for example, an atomic absorption measuring device.

At this time, the higher the concentration of the impurity in the solution is, the more the sensitivity of the measurement is improved. Therefore, in the case where an extremely small amount of impurities are measured, it is necessary to decrease an amount of the solution to minimum amount. However, in the above method, since a comparatively large amount of the solution 4, namely, at least about 10 ml is required for dissolving the substrate 10, the impurity concentration becomes low and thus the sensitivity was not so high.

For this reason, in order to improve the sensitivity of the measurement, after the semiconductor substrate or the thin film on the semiconductor substrate is dissolved, a method of concentrating the solution is used for measuring impurities contained in the solution. However, this method requires a long time for the concentration, and the solution might be possibly contaminated by more impurities during the concentrating process.

Furthermore, in the case where impurities in a silicon substrate are measured, the silicon substrate is dissolved by a volatile solution such as fluoric acid, and the dissolved silicon substrate is changed into fluoride silicon having volatility. As a result, the silicon can be easily removed, and thus the impurities can be measured easily. However, since it is difficult to remove materials such as Al and Ti other than the silicon, a very small impurities contained in an Al thin film and a Ti thin film could not be measured.

In addition, as the diameter of the semiconductor substrate is increased, a larger amount of solution and longer time are required for dissolving the semi-conductor substrate or the thin film on the semi-conductor substrate. Moreover, there arises a problem that time required for concentrating a lot of solutions becomes longer.

As mentioned above in the conventional impurity measuring method and impurity measuring device, since it is necessary to concentrate the solution in order to measure a very small of impurities, a longer time is required for the concentration, and the solution might be contaminated by impurities during the concentration. As another problem, since materials such as Al and Ti other than silicon are not removed, impurities contained in the Al thin film and the Ti thin film cannot be measured.

SUMMARY OF THE INVENTION

The present invention has been achieved under the above mentioned circumstances, and it is an object of the present invention to provide an impurity measuring method and an impurity measuring device which are capable of measuring a very small of impurities existing in a sample or on a surface of the sample at high sensitivity.

In order to solve the above mentioned problems and to achieve the above mentioned object, an impurity measuring method of the present invention is characterized by comprising the step of dissolving impurities which exist in a sample or on a surface of the sample and the sample in a solution by bringing the solution into contact with the surface of the sample; the step of putting a plurality of electrodes in the solution so as to apply a voltage across the electrodes; the step of depositing the impurities on a surface of the electrodes; and the step of analyzing the deposited impurities so as to measure the impurities.

In addition, an impurity measuring method of the present invention is characterized by comprising the step of dissolving impurities which exist in a sample or on a surface of the sample and the sample in a first solution by bringing the surface of the sample contact with the first solution; the step of putting a plurality of electrodes into the first solution so as to apply a voltage across the electrodes; the step of depositing the impurities on the surfaces of the electrodes; the step of dissolving the deposited impurities in a second solution; and the step of measuring the impurities dissolved in the second solution.

In addition, an impurity measuring device of the present invention is characterized by having means for soaking a sample in a solution for dissolving impurities which exist in the sample or on a surface of the sample, and the sample therein; a plurality of electrodes which are put into the solution; means for applying a voltage, which deposits the impurities dissolved in the solution on surfaces of the electrodes, across the plurality of electrodes; and means for detecting the deposited impurities.

The applying voltage may be such that the applying voltage deposits impurities to be measured but does not deposit the other impurities which are expected to be dissolved in the solution.

The applying voltage may be such that the applying voltage deposits only impurities to be measured and does not deposit the sample dissolved in the solution.

The applying voltage may be such that the applying voltage has a potential difference which is the same as or larger than a potential difference required for depositing the impurities to be measured.

In the step of dissolving the impurities and the sample in the solution or in the step of depositing the impurities on the surfaces of the electrodes, the solution may be stirred by a stirring device.

In the step of dissolving the impurities and the sample in the solution or in the step of depositing the impurities on the surfaces of the electrodes, an ultrasonic wave may be generated in the solution by an ultrasonic wave unit.

In the step of dissolving the impurities and the sample in the solution, or in the step of depositing the impurities on the surfaces of the electrodes, the solution may be heated by a heater.

In addition, an impurity measuring device of the present invention is characterized by having: means for soaking a sample in a first solution for dissolving the impurities, which exist in the sample or on a surface of the sample, and the sample therein; a plurality of electrode which are put into the first solution; means for applying a voltage, which deposits the impurities dissolved in the first solution on surfaces of the electrodes, across the plurality of electrodes; means for soaking the electrodes in a second solution for dissolving the deposited impurities; and means for detecting the impurities dissolved in the second solution.

As mentioned above, in the impurity measuring method of the present invention, two electrodes are put into the solution in which the impurities are dissolved, and the impurities are deposited on the surfaces of the electrodes by applying the voltage across the electrodes so that the deposited impurities are measured by a detector. For this reason, compared with the conventional method of directly measuring a solution in which impurities are dissolved, the sensitivity can be improved the method of the present invention.

In addition, since the impurity measuring method of the present invention makes it possible to obtain the enough high measuring sensitivity, the convention process of concentrating a solution is not required for improving the sensitivity. For this reason, it is possible to shorten the processing time required for the concentration greatly.

In addition, since it is not necessary to concentration a solution, such a problem that the solution is contaminated during the concentration and the accurate measuring becomes difficult can be avoided.

Moreover, in the impurity measuring method of the present invention, only desirable impurities can be deposited on a surface of electrodes by controlling a voltage to be applied across the electrodes put into a solution in which the impurities are dissolved. Also in the case where impurities, which exist in a film made of Al, for example, other than silicon film and on the surface of the film, as well as the Al film are dissolved, the material of the film is not deposited, and only the impurities to be measured can be deposited. Since a component such as Al does not have volatility, in the conventional method of concentrating a solution, a principle ingredient such as Al remains even when the solution is concentrated, and thus it is difficult to measure a very small amount of impurities. However, in the impurity measuring method of the present invention, since only the impurities to be measured can be deposited as mentioned above, a very small amount of impurities, which exist in a film made of Al, etc. other than a silicon film or on the surface of the film, can be measured.

In addition, in the impurity measuring method of the present invention of measuring impurities after the impurities deposited on the surfaces of the electrodes are dissolved in a solution, unlike the first solution which dissolves the sample and the impurities together, since the second solution dissolves only the impurities deposited on the surfaces of the electrodes, a great amount of the second solution is not required. For this reason, compared with the method of directly measuring the first solution, this method make it possible to further improve the sensitivity.

Furthermore, in this case, similarly to the method of directly measuring the deposited impurities, since it is not necessary to concentrate the first solution, the processing time can be shortened, and the possibility of contamination of the first solution can be eliminated. Moreover, a very small amount of impurities, which exist in a film made of Al, etc. other than a silicon film or on the surface of the film, can be measured.

In addition, in accordance with the impurity measuring device of the present invention, a sample is soaked in a solution so that impurities, which exist in the sample or a surface of the sample, and the sample are dissolved, and two electrodes are put into the solution and a voltage is applied across the electrodes. Then, the impurities dissolved in the solution are deposited on the surfaces of the electrodes, and the deposited impurities can be detected. As a result, a very small amount of impurities is measured accurately, and the processing time is shortened. Therefore, it is possible to measure a very small amount of impurities which exist in a film made of Al, etc. other than a silicon film or on the surface of the film.

In addition, in accordance with the impurity measuring device of the present invention, electrodes on which impurities are deposited are soaked in a second solution, and the impurities dissolved in the second solution can be detected. Therefore, a very small amount of impurities is measured at high sensitivity, and the processing time is shortened, thereby making it possible to measure a very small amount of impurities which exist in a film made of Al, etc. other than a silicon film or the surface of the film.

The electrodes may have a needle shape.

The means for soaking the sample in the solution may have a stirring device.

The means for soaking the sample in the solution may have an ultrasonic unit.

The means for soaking the sample in the solution may have a heater.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENT

Figure 1:
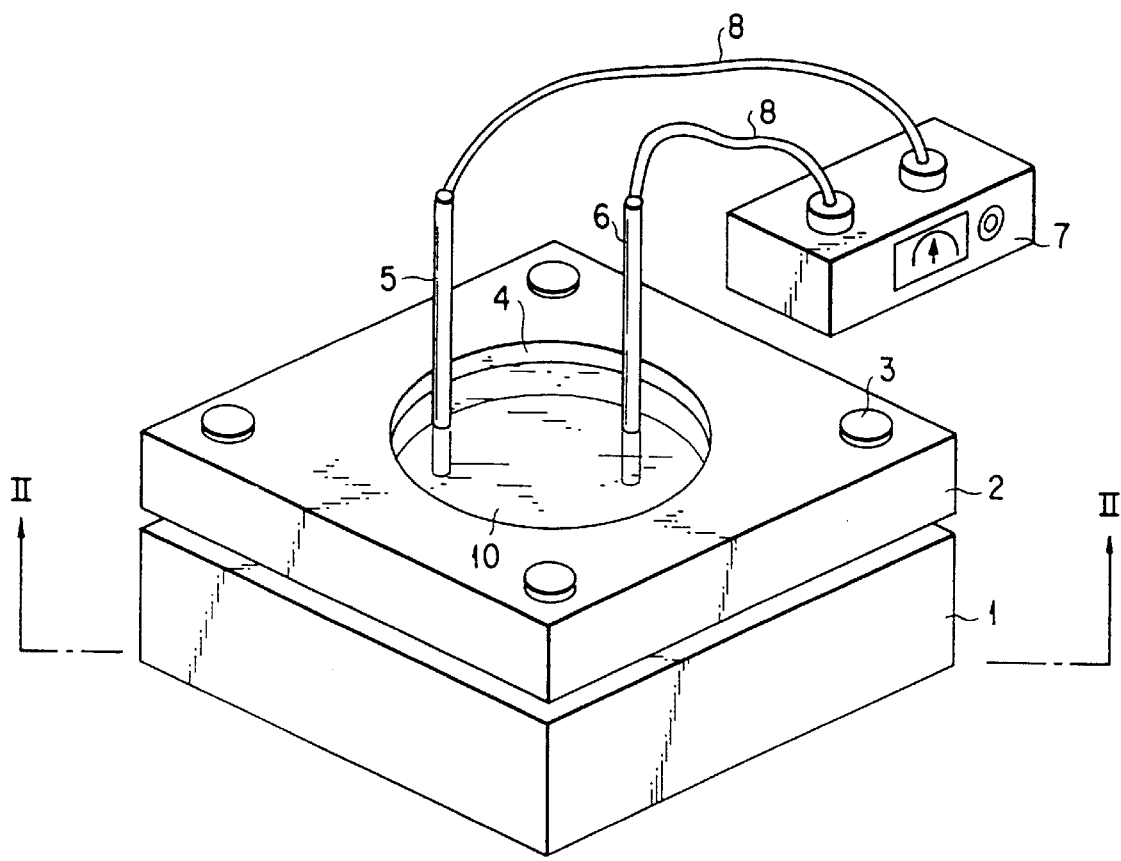
FIG. 1 is a perspective view which shows an arrangement of an impurity measuring device according to an embodiment of the present invention.

The following describes an embodiment of the present invention on referring to the drawings.

Figure 2:
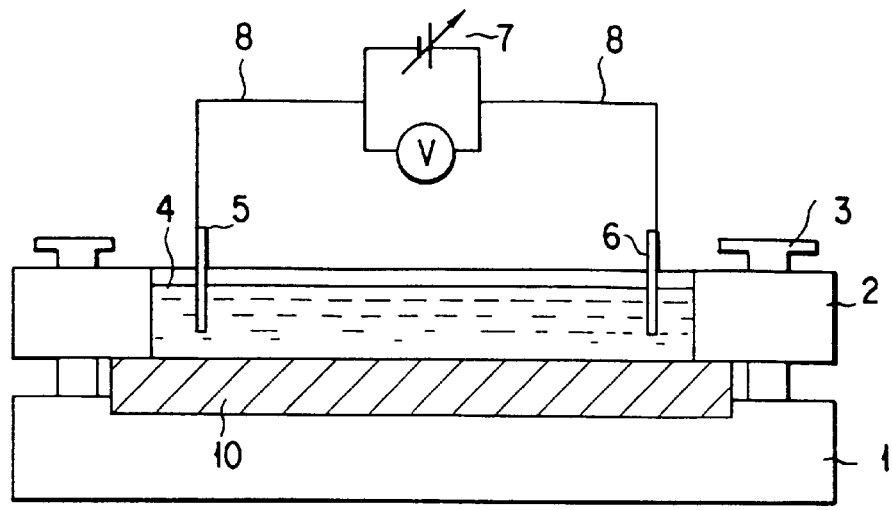
FIG. 2 is a cross sectional view taken along line II—II which shows the arrangement of the impurity measuring device in FIG. 1.

FIG. 1 is a shows an embodiment of an impurity measuring device of the present invention, and FIG. 2 is a cross sectional view taken along line II—II of the impurity measuring device in FIG. 1.

The impurity measuring device of the present embodiment is provided with a substrate holding stand 1, a frame 2 and four screws 3, like the conventional impurity measuring device. Moreover, the impurity measuring device is further provided with a working electrode 5, a counter electrode 6 to the working electrode 5, a potentiostat 7 and conductors 8 unlike the conventional device.

The substrate holding stand 1 has a concave section for holding a semiconductor substrate 10, and a depth of the concave section is smaller than a thickness of the semiconductor substrate 10. The frame 2 has an opening which penetrates the frame 2 at its center portion, and a diameter of the opening is smaller than a diameter of the semiconductor substrate 10. Moreover, the substrate holding stand 1 and the frame 2 respectively have holes for the screws 3 at their corners. The holding stand 1, the frame 2 and the four screws 3 are made of, for example, Teflon.

The working electrode 5 and the counter electrode 6 are formed by materials such as platinum which hardly reacts with a solution. Moreover, the working electrode 5 and the counter electrode 6 are respectively connected to electrode terminals of the potentiostat 7 by means of the conductors 8, and a voltage is applied across the working electrode 5 and the counter electrode 6 by the potentiostat 7.

The following explains a method of measuring a very small amount of impurities which exist in and on the semiconductor substrate and in and on a thin film formed on the semiconductor substrate by using the impurity measuring device of the present embodiment.

Like the conventional method, the semiconductor substrate 10, on which a film is not formed or a thin film is formed, is placed on the concave section of the holding stand 1, and the frame 2 is placed on the semiconductor substrate 10. Then, the corners of the frame 2 are fitted on the corners of the holding stand 1 and the corners are fastened by the screws 3 through the holes so that the frame 2 is fixed tight to the semiconductor substrate 10. Next, a solution 4, which dissolves the semiconductor substrate 10 or the thin film on the semiconductor substrate, is poured into a cavity which is formed by the opening of the frame 2 and the substrate 10 so that the semiconductor substrate 10 or the thin film on the semiconductor substrate is dissolved by the solution 4. When dissolved, impurities, which exist in and on the semiconductor substrate 10 or in and on the thin film formed on the semiconductor substrate, exist in the solution 4 as ion. The above-mentioned steps of the method are the same as the conventional method.

Then, unlike the conventional method, the working electrode 5 and the counter electrode 6 are put into the solution with them being separated from each other as shown in FIG. 1, and a voltage is applied across these electrodes by the potentiostat 7. The applied voltage varies with impurities to be measured and a substrate or a thin film to be dissolved, but its detail will be explained later. When the voltage is applied, the impurity starts to move in the solution 4 due to an electric field which is generated by the application of the voltage across the working electrode 5 and the counter electrode 6. The impurity ion, which got to the surface of the working electrode 5, receives electrons by the working electrode 5 according to a positive or negative electric charge of the ion, or electrons are discharged onto the working electrode 5 so as to be deposited on the surface of the working electrode 5.

Figure 3:
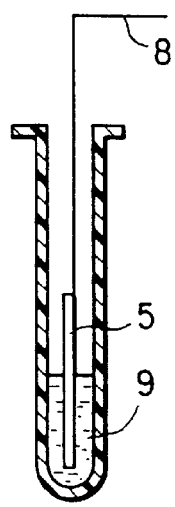
FIG. 3 is a view showing a working electrode 5 soaked in a solution 9, which is used for explaining an impurity measuring method of the present invention.
Figure 4:
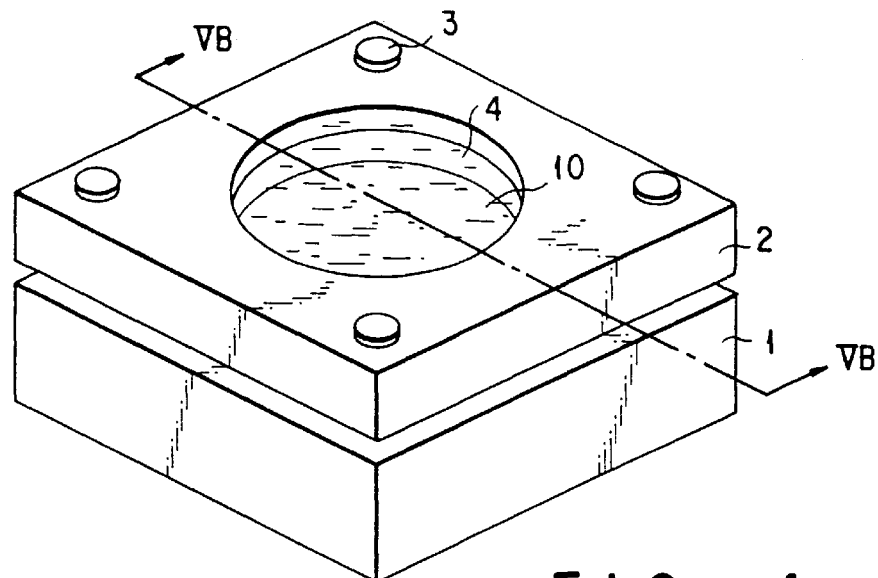
FIG. 4 is a perspective view which shows an arrangement of a conventional impurity measuring device.
Figure 5A:
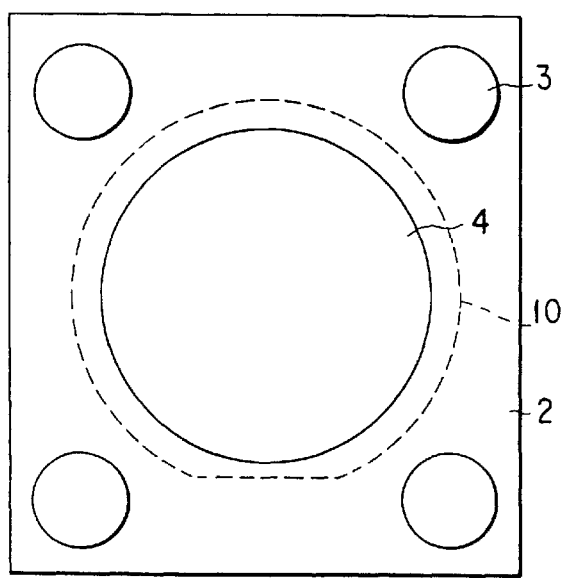
FIG. 5A is a top view which shows the arrangement of the impurity measuring device shown in FIG. 4.
Figure 5B:
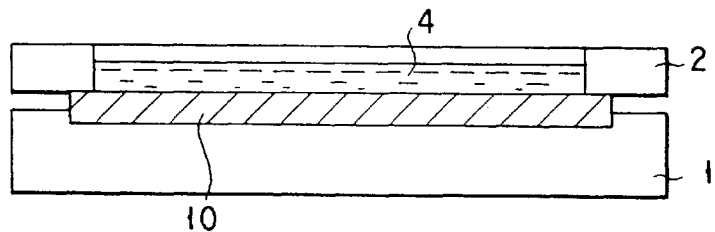
FIG. 5B is a cross sectional view taken along line VB—VB of FIG. 4.

Thereafter, the working electrode 5 is taken out of the solution 4, and the application of the voltage is stopped. Then, as shown in FIG. 3, the electrode 5 is soaked into a solution 9 contained in a vessel made of, for example, Teflon, which dissolves impurities to be measured, the impurities, which are deposited on the surface of the working electrode 5, are again dissolved. The impurities dissolved in the solution 9 are measured by, for example, a frame-less atomic absorption measuring device. At this time, in order to improve the sensitivity of the measurement, it is desirable that the concentration of the impurities in the solution 9 is high. For this reason, it is desirable that a minimum amount of the solution 9, which is required for dissolving the impurity coming out on the surface of the working electrode 5, is used. Moreover, in order to decrease the amount of the solution 9, it is desirable that the working electrode 5 has a needle-like shape.

The following details the case where metallic impurities in a silicon (Si) substrate and on a surface of the silicon substrate. First, the Si substrate is dissolved by using a mixed solution of fluoric acid and nitric acid as the solution 4. At this time, the dissolved Si exists in the solution 4 mainly as $SiF_6^{2-}$. Meanwhile, metallic impurities, which existed in the Si substrate and on the surface of the Si substrate, in the solution 4 as ions such as $Fe^{2+}$, $Cr^{3+}$, $Zn^{2+}$ and $Ni^{2+}$.

Table 1 shows a chemical reaction when each kind of impurity ions is deposited on the working electrode 5, and a reduction potential required for the working electrode 5 at the time of the deposition. The reduction potential is a potential when each kind of ions is deposited on the working electrode 5 in the case where a potential difference, which is larger than a certain potential of the counter electrode, is applied to the working electrode 5.

For example, when a positive potential of not less than 1.24 V is applied to the working electrode 5, Si is deposited on the working electrode 5. Moreover, for example, when a negative voltage, which is opposite to the counter electrode 6, is applied to the working electrode 5 so that the working electrode 5 has a potential difference of not less than 0.67 V, Cr is deposited on the working electrode 5. As shown in Table 1, typical impurities have a negative reduction potential, and only Si has a positive reduction potential. For this reason, when a negative voltage, which is opposite to the counter electrode 6, is applied to the working electrode 5, only impurities can be deposited on the working electrode, and thus it is possible to deposit Si on the working electrode 5.

As mentioned above, in the case where a potential difference, which is larger than reduction potential of the counter electrode 6, is applied to the working electrode 5, the impurity having the reduction potential is deposited. As is clear from Table 1, the reduction potential varies with a type of impurity ions. For this reason, an impurity to be deposited can be selected by suitably setting the applying voltage. For example, the case where a potential, which is 0.7 V lower than the counter electrode 6, is applied to the working electrode 5 is considered. In this case, since the reduction voltage of Zn is −0.76 V, namely, a potential difference is larger than 0.7 V, Zn is not deposited. However, since the reduction potential of Fe is −0.44 V, namely, the potential difference is smaller than 0.7V, Fe is deposited.

TABLE 1

| Chemical reaction on electrode | Reduction potential |
| --- | --- |
| $SiF_6^{2-} = 2e^- + Si + 6F$ | +1.24 V |
| $Cr^{3+} + 3e^- = Cr$ | −0.67 V |
| $Zn^{2+} + 2e^- = Zn$ | −0.76 V |
| $Fe^{2+} + 2e^- = Fe$ | −0.44 V |
| $Ni^{2+} + 2e^- = Ni$ | −0.228 V |

For example, in the case where Cr is deposited, the electrode 5 is soaked into the solution 9 which dissolves impurities such as nitric acid, and hydrochloric acid, and the impurities which are deposited on the electrode 5 are dissolved. Moreover, the impurities dissolved in the solution 9 are measured by using a frame-less atomic absorption measuring device, etc.

According to the above method, in order to dissolve the impurities deposited on the surface of the working electrode 5, for example, a small amount, i.e. about 1 ml of the solution 9 is sufficient. In such a manner, since the amount of the solution in which the impurities are dissolved can be reduced to about 1/10 of the conventional method, the concentration of the impurities in the solution becomes ten times as high as the conventional one, and thus the measuring sensitivity can be heighten to about 10 times.

In addition, in the conventional method, in order to improve the measuring sensitivity, since it is necessary to concentrate the solution, a longer time is required for the concentration, so the efficiency is unsatisfactory. However, in the method of the present invention, since the concentration of the impurities in the solution can be heightened without the concentration, the time required for the process before measurement can be shortened to about 1/10.

In addition, since the concentration is not required, there is no possibility of contamination of the solution during the concentration, thereby making it possible to analyze impurities as contaminants accurately.

In addition, the concentration of the impurities in the solution to be used for the measurement is determined by an amount of the solution 9 required for dissolving the impurities deposited on the working electrode 5, and it is not influenced by an amount of the solution 4 for dissolving the semiconductor substrate 10. For this reason, the measuring sensitivity is not influenced by the increase in the diameter of the semiconductor substrate. As the diameter of the semiconductor substrate 10 to be dissolved is increased, then a more amount of the solution 4 is required, and for this reason, in the conventional method, if an amount of impurities is constant, the concentration of the impurities in the solution 4 is lowered in accordance with the increase in the diameter of the semiconductor substrate, and thus the measuring sensitivity is lowered. Moreover, in the conventional method, in order to improve the measuring sensitivity, since it is necessary to concentrate a lot of the solution 4, the processing time becomes longer according to the increase in the diameter of the semiconductor substrate. Meanwhile, according to the present embodiment, as mentioned above, the measuring sensitivity is not influenced by the increase in the diameter of the semiconductor substrate. Furthermore, according to the present embodiment, as mentioned above, it is not necessary to concentrate the solution. For this reason, the processing time required before the measurement is not also influenced by the increase in the diameter of the semiconductor substrate. Namely, the shortening of the processing time in the present embodiment becomes more effective according to the increase in the diameter of the semiconductor substrate.

As the second embodiment, the following explains the case where impurities existing in an Al film are analyzed. First, the Al film is dissolved by using a mixed solution of hydrochloric acid, fluoric acid, nitric acid, etc. as the solution 4 composed of a solvent which dissolving an Al film. When the Al film is dissolved, Al exists in the solution 4 mainly as $Al^{3+}$, and its reduction voltage is −1.662 V. For this reason, when a voltage, which is −0.76 V more than and −1.662 V less than the counter electrode 6, is applied to the working electrode 5, the deposition of Al is suppressed, and thus only Cr, Zn, Fe and Ni to be measured can be deposited on the working electrode 5.

Thereafter, in the similar manner to the first embodiment, the impurities are again dissolved in the solution 9, and the impurities are measured by using the atomic absorption measuring device, etc.

In the second embodiment, in addition to the advantages of the first embodiment, further advantages are obtained. Namely, in the case where a very small amount of impurities existing in the Al film, for example, a lot of Al is dissolved in the solution 4 in the conventional method, and thus it is difficult to remove Al by using the volatile method, for example. For this reason, even if the solution 4 is concentrated, the concentration of Al also becomes higher, so it is difficult to measure a very small amount of impurities existing in the Al film. However, according to the present embodiment, only particular impurities of the impurities dissolved in the solution 4 can be selectively deposited by controlling a voltage to be applied to the working electrode 5. Namely, when a voltage which does not deposit, for example, Al but only impurities to be measured, is applied to the working electrode 5, impurities can be measured without any influence of Al. For this reason, a very small amount of impurities existing in a film other than, for example, silicon in the Al film can be measured.

The second embodiment explains the Al film as an example. However, even if a film is made of a material other than Al, when principle ingredients of a film are not reduced, and a voltage, which deposit only impurities to be measured, is applied across the working electrode 5 and the counter electrode 6, a very small amount of impurities can be measured at the high sensitivity without any influence of the principle ingredients.

In addition, in the first and second embodiments, after the impurities deposited on the working electrode 5 are dissolved again in the solution 9, the impurities are measured by using the atomic absorption measuring device, etc. However, the deposited impurities can be also directly measured by using a GD/MS (Grow Discharge Mass Spectroscopy) device, for example.

In such a method of directly measuring deposited impurities, since it is not necessary to dissolve the deposited impurities in the solution 9 again in such a manner as the embodiments, the operation becomes easy, and the processing time can be shortened. However, in general, the method of measuring impurities which have been dissolved in the solution 9 makes it possible to measure the impurities at higher sensitivity.

In addition to the method of the embodiments, when the semiconductor substrate 10 is dissolved in the solution 4, and impurities are deposited by applying a voltage across the electrode 5 and the counter electrode 6, the solution 4 can be stirred by using a stirring device such as a magnetic stirrer.

In addition, the solution 4 can be stirred by an ultrasonic wave by using an ultrasonic wave generator instead of the stirring device.

In addition, the solution 4 can be heated by using a heater instead of the stirring device.

In any methods of stirring, ultrasonic wave and heating, in addition to the effects of the first and second embodiments, the effect, which promotes the solution of the semiconductor substrate 10 into the solution 4 and the deposition of impurities on the working electrode 5, is produced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An impurity measuring device comprising:
   a frame adapted to be disposed on one surface of a substrate, the frame having an opening hole extending therethrough so that when the frame is disposed on the surface of the substrate a cavity is formed by the frame and said surface of the substrate, a first solution being poured into the cavity when the impurity measuring device is used to dissolve impurities existing on said surface of the substrate and within the substrate into the first solution;
   a plurality of electrodes which are put into the first solution in said cavity;
   a voltage supply for supplying a voltage across the electrodes to deposit the impurities dissolved in the first solution onto the electrodes;
   a vessel containing a second solution into which said electrodes with the impurities deposited thereon are soaked to dissolve the deposited impurities on the electrodes into the second solution; and
   a measuring unit for measuring the impurities dissolved in the second solution.

2. The impurity measuring device according to claim 1, wherein said electrodes have a needle shape.

* * * * *